United States Patent [19]

Sone et al.

[11] Patent Number: 5,091,511
[45] Date of Patent: Feb. 25, 1992

[54] LYMPHOKINE ACTIVATED KILLER SUPPRESSIVE FACTOR (LAKSF), PROCESS FOR PRODUCING IT AND IMMUNOSUPPRESSIVE AGENT COMPRISING IT

[75] Inventors: Saburo Sone, Tokushima; Masanobu Munekata; Akito Nakamura, both of Yaizu; Kiichi Uchida, Tokyo; Kazumaro Seto, Yaizu, all of Japan

[73] Assignee: Sapporo Breweries Limited, Tokyo, Japan

[21] Appl. No.: 411,846

[22] Filed: Sep. 25, 1989

[30] Foreign Application Priority Data

Oct. 3, 1988 [JP] Japan .................. 63-247509

[51] Int. Cl.⁵ .................. C07K 15/00; A61K 37/02
[52] U.S. Cl. .................. 530/351; 530/350; 530/827; 530/399; 530/395; 424/85.1; 424/85.2
[58] Field of Search .......... 530/351, 350, 827, 399, 530/395; 424/85.1, 85.2

[56] References Cited

U.S. PATENT DOCUMENTS 4,988,676  1/1991  Platsoucas .................. 530/351
5,037,958  8/1991  Hashimoto et al. ......... 530/351

FOREIGN PATENT DOCUMENTS 0179900  7/1988  Japan .................. 530/351

OTHER PUBLICATIONS

Owens et al, *EMBO* 3(5) 1984, pp. 945–952.
Almawi et al, *J. Immunol.*, 141, 1988, pp. 2529–2535.
Gulwani et al, *J. Immunol.*, 139, 1987, pp. 2130–2136.
Tanaka et al, CA vol. 99, 1983, #192883d.
Ebert et al, *J. Immunol.*, 138, 1987, pp. 2161–2168.
Lindemann et al, CA vol. 109, #33608b, 1988.
Nishimura et al, *J. Immunol.*, 142, 1989, pp. 2155–2161.
Chong et al, *J. Immunol.*, 141, 1988, pp. 4418–4424.
Ortaldo et al, *J. Immunol.*, 143, 1989, pp. 366–371.
Ibayashi, Y. et al., Cellular Immunology, 110, 365–378 (1987).
Mule, J. et al., Cancer Immunol. Immunother 26, 95–100 (1988).
Grimm, E. A. et al., Cancer Immunol. Immunother 27, 53–58 (1988).
Spits, H. et al., J. Immunol., 141, 29–36 (1988).
Sone, S. et al., J. Nat. Cancer Inst., 80, 425–432 (1988).

*Primary Examiner*—Garnette D. Draper
*Attorney, Agent, or Firm*—Frishauf, Holtz, Goodman & Woodward

[57] ABSTRACT

Lymphokine activated killer suppressive factor (LAKSF) and a process for producing the LAKSF by cultivating human mono-cytic cells for alveolar macrophages activated by a stimulator to produce LAKSF and harvesting it. The LAKSF has a LAK induction suppressive activity and an immunosuppressive effect and thus the LAKSF is useful as a medicine.

11 Claims, 3 Drawing Sheets

LYMPHOKINE ACTIVATED KILLER SUPPRESSIVE FACTOR (LAKSF), PROCESS FOR PRODUCING IT AND IMMUNOSUPPRESSIVE AGENT COMPRISING IT

BACKGROUND OF THE INVENTION

A good deal of attention has been attracted to adoptive immunotherapy with lymphokine activated killer cells (LAK) as highly efficient cancer therapy, which was developed by S. A. Rosenberg et al. Since the study on the mechanism of LAK regulation was recently initiated, the means of enhancing or suppresing LAK activity was hardly studied, although LAK and CTL (cytotoxic T lymphocytes) are considered to participate also in rejection transplanted organs and in autoimmune diseases. Rosenberg et al. recently reported that transforming growth factor-$\beta$ (TGF$\beta$) suppresses generation of LAK and CTL (Cancer Immunol. Immunother., 26, 45, 1988). However, TGF$\beta$ stimulate the growth of certain tumor cells and it cannot be used as a medicine for human immune diseases.

SUMMARY OF THE INVENTION

The present invention relates to novel lymphokine activated killer suppressive factor (hereinafter referred to as "LAKSF"), a process for producing it, and an immunosuppressive agent comprising it as an effective ingredient.

DETAILED DESCRIPTION OF THE INVENTION

Figure 1:
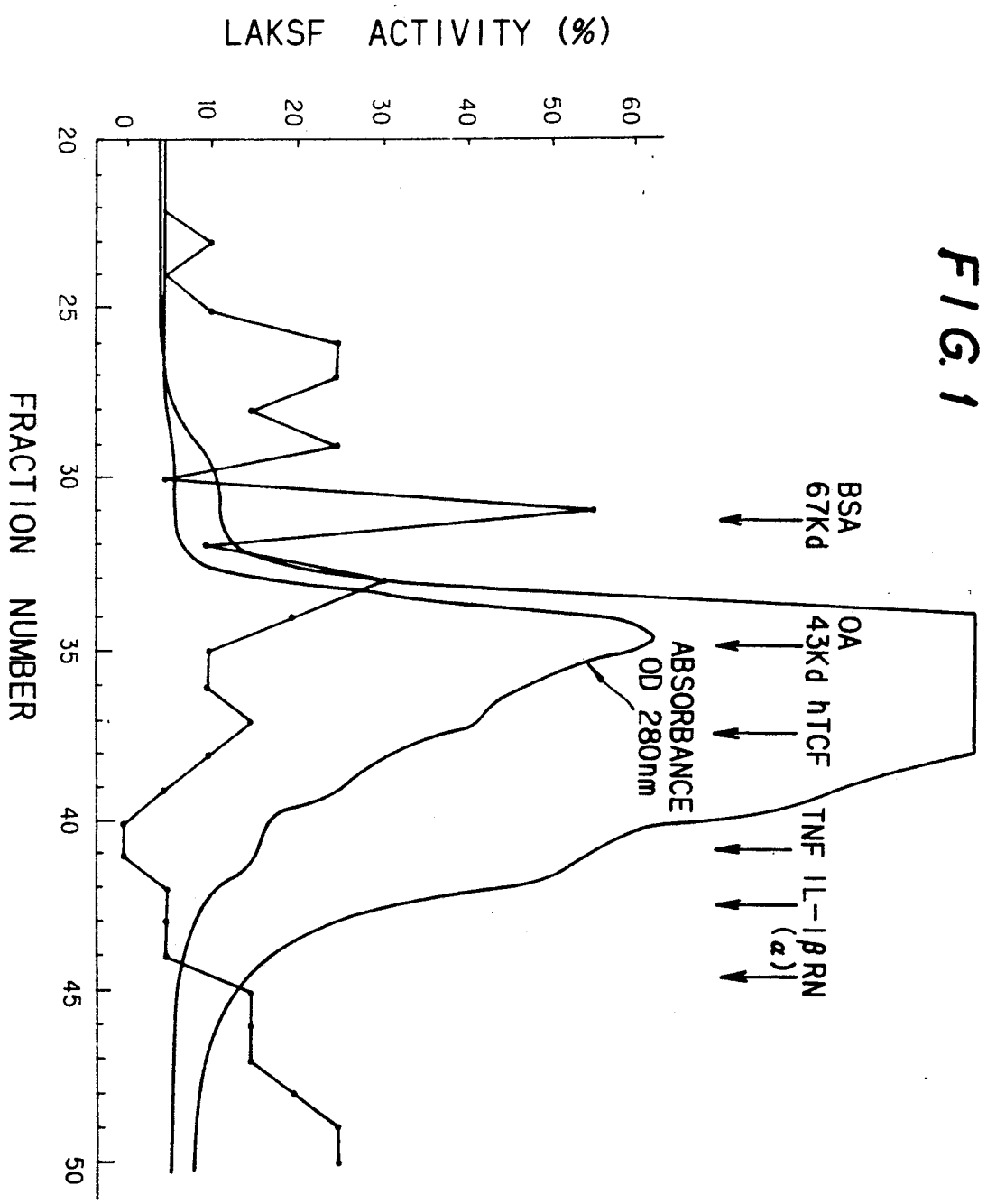
FIG. 1 shows the elution pattern of high performance liquid chromatography of TSK-G3000SW in Example 1. Arrows in the figure mean BSA (bovine serum albumin, molecular weight 67,000), OA (ovalbumin, molecular weight 43,000), RN (ribonuclease A, molecular weight 13,700), TNF (recombinant human tumor necrosis factor, molecular weight 17,000), and IL-1$\beta$ (recombinant human interleukin 1$\beta$, molecular weight 17,300) used as molecular weight marker. Black spots with a solid line (    ) shows LAKSF activity (% control). The cross axis shows fraction number (1 fraction: 4.2 ml).

As the result of keen investigation for solving said problem, the present inventors have found that a novel bioactive substance can be produced in vitro by activated human alveolar macrophages or monocytic cells derived from human peripheral blood. Good stimulants for activation are lipo-polysaccharide derived from *Escherichia coli* and muramyldipeptide, a fundamental structure unit the peptide glycan of Mycobacterium.

This novel bioactive substance LAKSF inhibited in vitro LAK induction from human or mouse lymphocytes due to interleukin-2 (IL-2), depending upon its concentration. The LAKSF of this invention was found to be different from TGF$\beta$ without neutralization of its activity by an anti-TGF$\beta$ antibody. Further, it was found that its biological activities are different from those of known monokines, TNF, IL-1$\alpha$, IL-$\beta$, LT, TCF, IFN$\alpha$, IFN$\beta$ and IFN$\gamma$ and is not neutralized by antibodies to these monokines. Therefore, the present substance is a novel bioactive substance.

The present invention has been established on the basis of such findings and relates to a LAKSF having a molecular weight of 68,000±5,000 (measured by gel filtration) and an isoelectric point of pH 6.8±0.5. Particularly, this invention is directed to the process for producing said LAKSF which comprises cultivating human derived monocytic cells or alveolar macrophages activated by a stimulator to produce LAKSF and harvesting it and to an immunosuppressive agent comprising said LAKSF as an effective ingredient.

The LAKSF of the present invention can be obtained by cultivating monocytic cells derived from human peripheral blood or alveolar macrophages in the presence of stimulators and harvesting culture supernatant. The human monocytic cells employed in the present invention may be prepared by subjecting leukocytes, obtained by taking peripheral blood of healthy humans or leukopheresis, to counterflow centrifugal elutriation with a Hitachi Koki SRR-6Y elutriater to get a monocyte suspension of a purity of more than 95% or by isolating mononuclear leukocytes by a lymphocyte separation medium (LSM) and subjecting them to percoll gradient centrifugation to isolate monocytes. Normal alveolar macrophages are prepared by inserting a fiber-optic bronchoscope into the lungs of healthy humans, washing the lungs with sterilized 0.9% NaCl solution, centrifuging the cell suspension and collecting adherent cells.

These monocytes and alveolar macrophages can be ordinarily cultured in a medium containing bovine serum as well as in a serum-free medium or in a chemically defined medium.

The stimulator employed in the present invention includes conditioned media of human tumor cells, chemical substances or natural extracts to induce the differentiation of monocytic cells and their combination. The chemical substances or natural extracts to induce differentiation of monocytes means so-called macrophage activators, such as muramyldipeptide (MDP), 12-o-tetradecanoylphorbol-13-acetate (TPA) and dimethyl sulfoxide (DMSO).

A further potent stimulator is an endotoxin obtained from Gram negative or positive bacteria, including lipopolysaccharide derived from *Escherichia coli*, Pseudomonas or Salmonella. Lipopolysaccharide of Gram-positive bacteria can also be used.

The LAKSF of the present invention can be induced by cultivating human monocytic cells or alveolar macrophages in normal culture media such as RPMI1640 medium supplemented with bovine serum with a stimulator. In general, said cells are cultivated in usual culture condition for 4 to 24 hours in the presence of 0.1 to 10 $\mu$g/ml of a stimulant such as lipopolysaccharide from *Escherichia coli*, whereby the LAKSF can be secreted into culture supernatant.

LAKSF can be purified and isolated by combining well-known purification methods, for example, dialysis, salting-out filtration, centrifugation, concentration, lyophilization, etc. When a highly purified LAKSF is needed, additional means such as gel filtration chromatography, ion exchange chromatography, affinity chromatography, isoelectric-forcusing, hydroxyapatite column chromatography and the like can be adopted in combination. In general, the culture supernatnat containing the LAKSF is collected by centrifugation, concentrated by ultrafilter apparatus (Millipore Immersible CX-10, Amicon Diaflow Membrane YM-10, Amicon Hollow Fiber P-10, etc.), dialyzed with 0.05M phosphate buffer (pH 7, containing 0.12M sodium chloride), and applied to crosslinked dextran gel filtration column, eluting with 0.05M phosphate buffer (pH 7, containing 0.12M sodium chloride), whereby we obtained active fractions (hereinafter referred to as "LAKSF active fractions") to inhibit the LAK induction of human peripheral blood lymphocytes and mouse spleen cells due to IL-2 (assayed by measuring cytotoxic activity). The fractions are concentrated with an ultrafilter apparatus and subjected to HPLC liquid gel filtration chromatography (TSK.G3000SW etc.), eluting with 0.05M phosphate buffer (pH 7, containing 0.03M sodium chloride), whereby the LAKSF active fraction of molecular weight of 68,000±5,000 is obtained. After concentration with an ultrafilter apparatus, the active solution is subjected to ampholine column isoelectric forcusing (1% ampholyte, pH 3.5–10, 900 V, 40–48 hours) to get the LAKSF active fraction of an isoelectric point of 6.8±0.5. If more purified LAKSF were needed, contaminated serum glycoprotein in active fractions can be prepared from LAKSF by ConA-sephalose chromatography. Moreover, LAKSF can be isolated by using ion exchange chromatography or hydroxyapatite column chromatography.

LAKSF of the present invention thus produced and purified has the following physicochemical properties.

(1) Molecular weight

This substance shows a relative molecular weight of 68,000±5,000 according to the gel filtration molecular sieving method (TSK.G3000SW, Sephadex G-200 etc.).

(2) Isoelectric point

This substance shows an isoelectric point of 6.8±0.5 according to ampholine column isoelectric forcusing.

(3) Thermostability

This substance is inactivated by heating at 70° C. for 30 minutes.

(4) Stability against enzymes

This substance is inactivated by treating with protease.

(5) Neutralization with antibodies to various cytokines

LAKSF activity was not inactivated with anti-human TNF antibody, anti-human IL-1$\alpha$ antibody, anti-human IL-1$\beta$ antibody, anti-human LT antibody, anti-human TGF$\beta$ antibody, and anti-human IL-4 antibody. Accordingly, it is confirmed that the LAKSF is not human TNF, IL-1$\alpha$, IL-1$\beta$, LT, TGF$\beta$ or IL-4 (Table 1).

TABLE 1

| | Neutralizing test of LAKSF activity with antibodies to various cytokines | | | | | | |
|---|---|---|---|---|---|---|---|
| | LAKSF activity (Unit/ml, human LAK system) | | | | | | |
| Antibody treatment | No-treatment | Anti-hTGF$\beta$ antibody | Anti-hTNF antibody | Anti-hIL-1$\alpha$ antibody | Anti-hIL-1$\beta$ antibody | Anti-hLT antibody | Anti-IL-4 antibody |
| LAKSF (1 Unit/ml) | 1 | 1 | 1 | 1 | 1 | 1 | 1 |
| hTGF$\beta$ (0.2 ng/ml) | 1 | 0 | 1 | 1 | 1 | 1 | 1 |
| hTNF (100 Unit/ml) | 0 | n.d. | n.d. | n.d. | n.d. | n.d. | n.d. |
| hIL-1$\alpha$ (1 Unit/ml) | 0 | n.d. | n.d. | n.d. | n.d. | n.d. | n.d. |
| hIL-1$\beta$ (1 Unit/ml) | 0 | n.d. | n.d. | n.d. | n.d. | n.d. | n.d. |
| hLT (100 Unit/ml) | 0 | n.d. | n.d. | n.d. | n.d. | n.d. | n.d. |
| hIL-4 (100 Unit/ml) | 1 | 1 | 1 | 1 | 1 | 1 | 0 | n.d.: Not done
Units of hTNF, hIL-1$\alpha$, hIL-1$\beta$, hLT and hIL-4 were shown by the respective biological activity unit.

(6) Cytotoxic activity

The LAKSF does not show directly cytotoxic activity to A375, L929 and the like cells as seen in TCF, TNF, LT, and IL-1. Accordingly, LAKSF is not TCF.

(7) Antiviral activity

The LAKSF does not show antiviral activity as seen in IFN$\alpha$, IFN$\beta$ and IFN$\gamma$. Accordingly, LAKSF is not IFN.

(8) IL-2 inhibitor activity

The LAKSF has no IL-2 inhibitor activity. It does not inhibit the growth of ConA-activated T cell in response to IL-2. Further, addition of excessive IL-2 didn't cancel the suppressive activity of the LAKSF, and had an inclination to increase the inhibitory activity.

(9) Time course of suppression for LAK induction by LAKSF

The LAKSF acted at the beginning of LAK induction, and conferred about 50% inhibition by 4 hours incubation and almost maximal inhibition by 8 hours.

The LAKSF of the present invention showed lymphokine activated killer (LAK) suppressive activity as follows:

1. Human LAK induction suppressive activity (in vitro)

LAK was induced by cultivating human lymphocytes in the presence of human IL-2, and LA activity was assayed by using $^{51}$Cr labeled Daudi cells. Cytotoxity was determined by the amount of $^{51}$Cr released from dead target cells. LAK suppressive activity means percent inhibition of the cytotoxic activity of LAK cell treated with the LAKSF. In general, mononuclear cells (MNC) were separated from human peripheral blood and removing monocytes from MNC by plating in a plastic schale for 2 hours to obtain purified lymphocytes. Lymphocytes (0.5 to $2.0 \times 10^6$ cells/ml), human recombinant IL-2 (IU/ml) and sample were plated in 96 wells microtiter plates. RPMI-1640 medium supplemented with 5% FBS was used. The number of lymphocytes was changed depending upon E/T (Effector target ratio). LAK cells are induced by cultivating in humidified atmosphere at 37° C. in 5% carbon dioxide for 4 days. Microtiter plates are centrifuged at 1000 rpm for 5 minutes at the end of the culture. After removal of supernatant, 100 μl of medium and $1 \times 10^4$ cells of $^{51}$Cr-labelled Daudi cells in 100 μl of medium are added to each well. Plates are centrifuged at 500 rpm for 5 minutes to bring target cells into contact with lymphocytes. Plates are in ordinary condition for 4 hours. After microtiter plates are centrifuged at 1000 rpm for 5 minutes, 100 μl of the supernatant are removed from each well, and radioactivity was determined by a γ counter.

LAK activity is calculated according the following equation.

$$LAK \text{ activity } (\%, \text{ specific lysis}) = \frac{\text{Experimental release} - \text{Spontaneous release}}{\text{Maximum release*} - \text{Spontaneous release}} \times 100$$

$$LAKSF \text{ activity } (\%) = \left(1 - \frac{LAK \text{ activity in the presence of a sample}}{LAK \text{ activity in the absence of a sample}}\right) \times 100$$

*Maximum release was determined by lysis of $^{51}$Cr-labelled target cells in 1N HCl.
**50 μl of a medium is added in place of a sample.

Biological activity necessary for showing 50% LAKSF activity is defined as 1 Unit.

2. Mouse LAK induction suppressive activity

Nylon wool-passed splenocytes were used as lymphocytes. One unit/ml of r-hIL-2 (Takeda Chemical Industries) was used as in human case for LAK induction. P815 and EL4 were used as a target cell.

For employing the LAKSF produced by the present invention as a medicine, it is administered in the appropriate form to express LAK suppressive activity and immunosuppressive effects. As an ordinary administration route, the LAKSF can be intravenously, subcutaneously or intramuscularly administered to patients in a solution in sterilized isotonic saline or the like. In that case, human serum albumin, mannitol or the like is added as a stabilizer.

According to the present invention, novel lymphokine activated killer suppressive factor (LAKSF) can be produced effectively in vitro monocyte culture. The LAKSF of this invention is useful as a medicine, showing a LAK induction suppressive activity and an immunosuppressive effect.

Presently preferred and practical embodiments of the present invention are illustratively shown in the following examples.

EXAMPLE 1

Peripheral blood (10 liter) of healthy persons was collected, and monocytes were separated by LSM. These monocytes were subjected to continuous centrifugation with elutriater rotator (Hitachi SRR6Y rotator, Beckman JE-6B etc.) to get $2 \times 10^8$ monocytes with a purity of above 95%. Monocytes ($2 \times 10^5$ cells/ml) were suspended in RPMI1640 medium supplemented with 2% fetal calf serum containing 1 μg/ml lipopolysaccharide from Escherichia coli and cultivated in polystyrene centrifugal tubes or rotary culture bottles at 37° C. for 16 hours.

After 16 hours, the cell-free supernatants were harvested by centrifugation and filtered through a membrane filter (pore diameter 0.45 μm) to obtain 1.0 liter of crude LAKSF solution. This solution was concentrated by ultrafiltration (Millipore immersible CX10, Amicon YM-10 etc., nominal molecular weight limit 10000) to 10 ml. Then, the concentrate was applied to a column (5 cm of diameter, 75 cm of height) of cross-linked dextran (LKB Ultrogel AcA34 etc.) equilibrated with 0.05M phosphate buffer (pH 7, containing 0.12M sodium chloride), and eluted with 0.05M phosphate buffer (pH 7, containing 0.12M sodium chloride) at a flow rate of 20 ml/hour Each 10 ml of fraction was collected, and a LAKSF active fraction (Fraction No. 110-115) was obtained.

Figure 2:
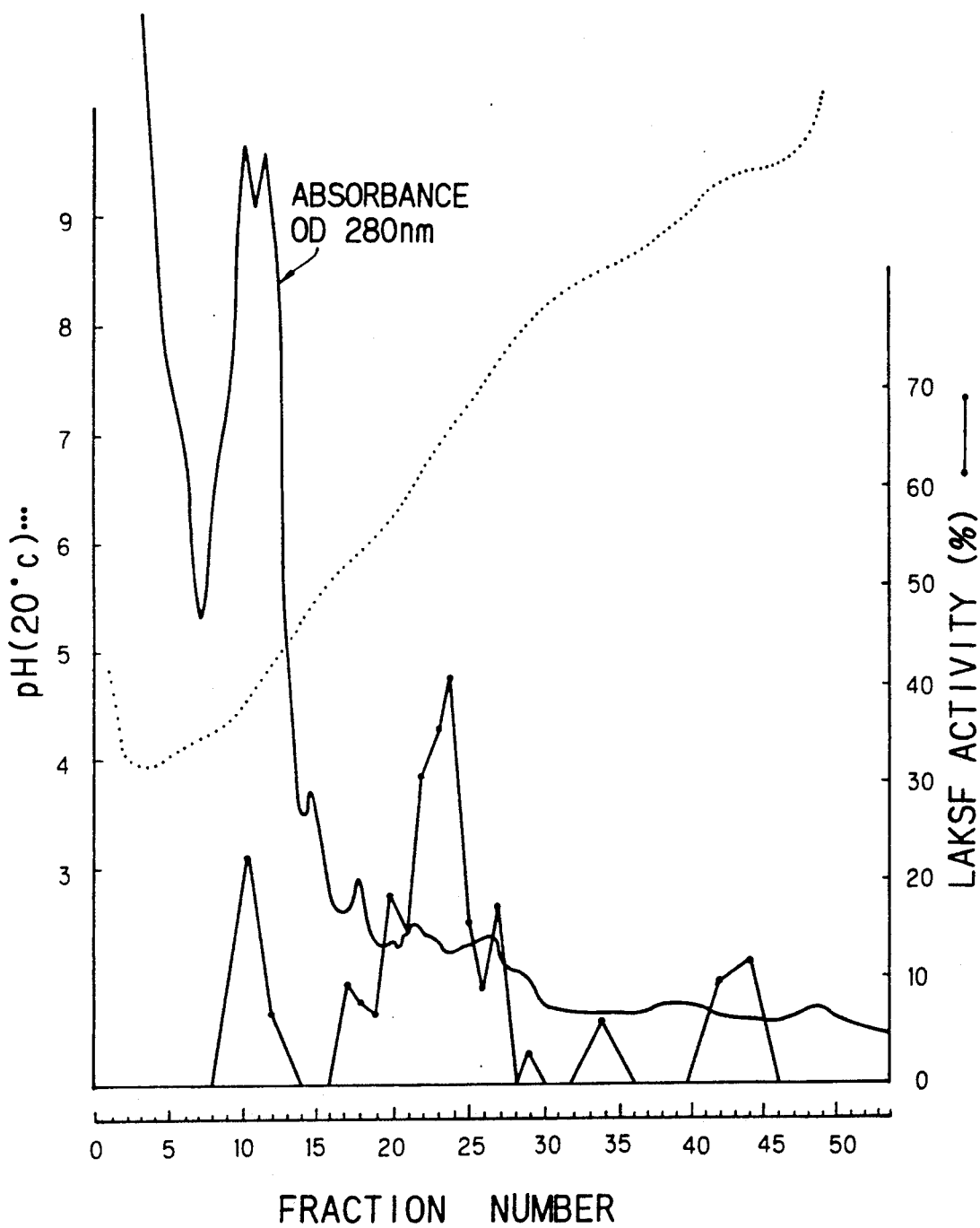
FIG. 2 shows the elution pattern of Ampholine column isoelectric focusing in Example 1. Black spots with a solid line (    ) shows LAKSF activity (% control), and the dotted line (----------) shows pH gradient.

Said fraction was concentrated with an ultrafilter to 2 ml, and the concentrate was applied twice by 1 ml into high performance liquid gel filtration chromatography (TSK-G3000SW etc., $\phi 2.15 \times 60$ cm), eluting with 0.05M phosphate buffer (pH 7, containing 0.03M sodium chloride) at a flow rate of 1.4 ml/minute. The fraction was separated by 4.2 ml to obtain LAKSF fractions (Molecular weight 68,000±5,000) (see FIG. 1). The LAKSF fraction was concentrated with an ultrafilter to 6 ml and subjected to an Ampholine column isoelectric forcusing apparatus at 2° C. 900 V for 48 hours. Fractions of pI 6.8±0.5 suppressed LAK induction (see FIG. 2).

Figure 3:
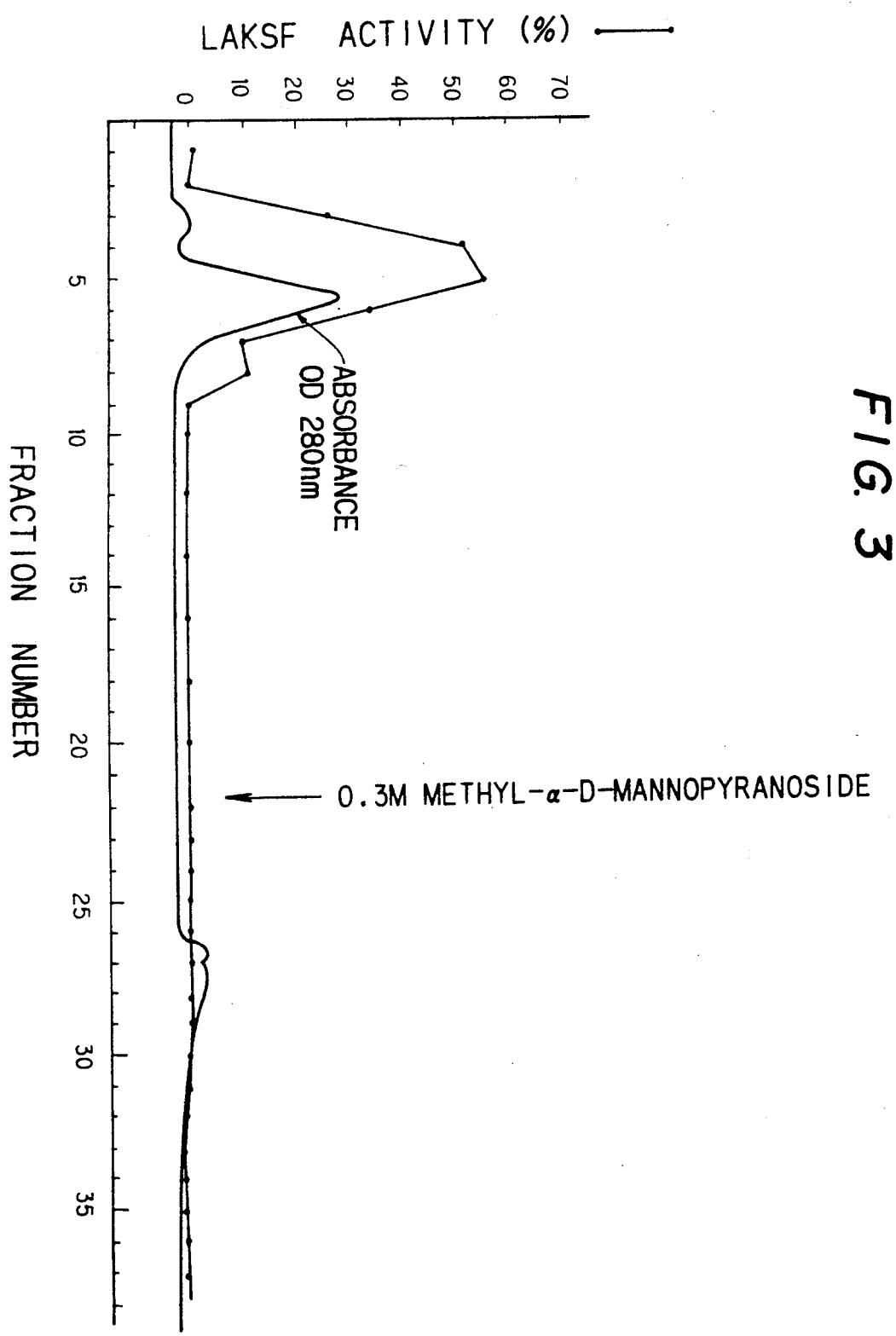
FIG. 3 shows the elution pattern of ConA-Sepharose affinity chromatography in Example 1. Black spots with a solid line (    ) shows LAKSF activity (% control).

This LAKSF active fraction was concentrated with an ultrafilter to 1 ml, and applied to a ConA-Sepharose column (10 ml, $\phi 1.5 \times 6$ cm column) equilibrated with 50 mM tris-HCl buffer (pH 7.7, containing 0.1M sodium chloride, 1 mM calcium chloride and 1 mM magnesium chloride). The column was eluted with the same buffer at the rate of 20 ml/hour. Non-adsorbed material was eluted with 40 ml buffer, and the adsorbed glucoprotein was eluted with 50 mM tris-HCl buffer (pH 7.7) containing 0.3M methyl α-D-mannopyranoside. LAKSF activity was observed in the fraction which was not adsorbed on ConA-Sepharose (see FIG. 3). At this the time specific activity was $3 \times 10^4$ unit/mg protein.

What is claimed is:

1. An isolated and substantially pure lymphokine activated killer suppressive factor having a molecular weight of 68,000±5,000 as measured by gel filtration and an having isoelectric point of pH 6.8+0.5.

2. The lymphokine activated killer suppressive factor according to claim 1, wherein the lymphokine activated killer suppressive factor is inactivated by heating at 70° C. for 30 minutes.

3. The lymphokine activated killer suppressive factor according to claim 1, wherein the lymphokine activated killer suppressive factor is inactivated by treating said factor with protease.

4. The lymphokine activated killer suppressive factor according to claim 1, wherein the lymphokine activated killer suppressive factor is not inactivated with anti-human TNF antibody, anti-human IL-1α antibody, anti-human IL-1β antibody, anti-human LT antibody, anti-human TGFβ antibody or anti-human IL-4 antibody.

5. The lymphokine activated killer suppressive factor according to claim 1, wherein the lymphokine activated killer suppressive factor is not TCF.

6. The lymphokine activated killer suppressive factor according to claim 1, wherein the lymphokine activated killer suppressive factor is not IFN.

7. The lymphokine activated killer suppressive factor according to claim 1, wherein the lymphokine activated killer suppressive factor has no IL-2 inhibitor activity.

8. The lymphokine activated killer suppressive factor according to claim 1, wherein the lymphokine activated killer suppressive factor has lymphokine activated killer suppressive activity.

9. The lymphokine activated killer suppressive factor according to claim 1, wherein the lymphokine activated killer suppressive factor is inactivated by heating at 70° C. for 30 minutes, is inactivated treating said factor with protease, is not inactivated with anti-human TNF antibody, anti-human IL-1α antibody, anti-human IL-1β antibody, anti-human LT antibody, anti-human TGFβ antibody or anti-human IL-4 antibody, is not TCF, is not IFN, has no IL-2 inhibitor activity and has lymphokine activated killer suppressive activity.

10. An immunosuppressive composition comprising an immunosuppressive effective amount of a lymphokine activated killer suppressive factor having a molecular weight of 68,000±5,000 as measured by gel filtration and having an isoelectric point of pH 6.8±0.5 as an effective ingredient and a therapeutically or pharmaceutically acceptable carrier.

11. The composition according to claim 10, wherein the carrier is a sterilized isotonic saline solution.

* * * * *